United States Patent [19]

Iwaya et al.

[11] Patent Number: 5,032,390
[45] Date of Patent: Jul. 16, 1991

[54] ANTI-SUNTAN COSMETIC COMPOSITION

[75] Inventors: Katsumasa Iwaya, Oyama; Hajime Hotta, Funabashi, both of Japan

[73] Assignee: Kao Corporation, Tokyo, Japan

[21] Appl. No.: 449,059

[22] Filed: Dec. 18, 1989

Related U.S. Application Data

[63] Continuation of Ser. No. 941,341, Dec. 15, 1986, abandoned.

[30] Foreign Application Priority Data

Dec. 18, 1985 [JP] Japan ................... 60-284579

[51] Int. Cl.⁵ .............. A61K 7/027; A61K 7/42; A61K 7/48; A61K 9/10
[52] U.S. Cl. .................... 424/59; 424/63; 424/64; 424/69; 514/844; 514/845; 514/847; 514/937
[58] Field of Search ............................ 424/59

[56] References Cited

U.S. PATENT DOCUMENTS

| | | | |
|---|---|---|---|
| 2,175,213 | 10/1939 | Parsons | 424/59 |
| 3,392,040 | 7/1968 | Kass | 424/59 X |
| 3,697,642 | 10/1972 | Madigan | 424/59 |
| 4,431,673 | 2/1984 | Goldner et al. | 424/59 |
| 4,578,266 | 3/1986 | Tietjen et al. | 424/DIG. 5 |

FOREIGN PATENT DOCUMENTS

| | | | |
|---|---|---|---|
| 4742502 | 10/1972 | Japan | 424/59 |
| 0231607 | 11/1985 | Japan | 424/59 |

OTHER PUBLICATIONS

Goodman, Cosmetic Dermatology, 1936, pp. 509, 528, 529 and 532.

Primary Examiner—Dale R. Ore
Attorney, Agent, or Firm—Oblon, Spivak, McClelland, Maier & Neustadt

[57] ABSTRACT

A novel anti-suntan cosmetic composition comprises from 1 to 25% by weight of fine particulate zinc oxide having an average particle size of from 70 to 300 mμ, which scatters or absorbs ultraviolet rays, especially those in UV-A region.

The composition prevent human skin from blotches and freckles, and supress the aging of the skin.

6 Claims, 6 Drawing Sheets

A: Zinc oxide (0.5μ)   B: Ferric oxide (0.5μ)   C: Titanium oxide (0.4μ)

a: Titanium oxide having an average particle size of about 15 mµ
b: 〃 35 mµ
c: 〃 50 mµ
d: 〃 75 mµ
e: 〃 200 mµ

A: Titanium oxide treated by metal soap
B: Titanium oxide treated by silicone oil
C: Non-treated titanium oxide

ANTI-SUNTAN COSMETIC COMPOSITION

This is a continuation of application Ser. No. 06/941,341, filed on Dec. 15, 1986, now abandoned.

BACKGROUND OF THE INVENTION

1. Field of the Invention

This invention relates to an anti-suntan cosmetic composition and, more particulary, to an anti-suntan cosmetic composition comprising a specific zinc oxide which scatters or absorbs ultraviolet rays, especially those in UV-A region, harmful to the skin. The skin can be protected from suntan by the anti-suntan cosmetic composition, so that the skin would not be blotched or freckled and also be prevented from aging.

2. Description of the Prior Art

As an anti-suntan cosmetic composition, ultraviolet absorbers or titanium oxide having specific particle size have been conventionally used. Such anti-suntan cosmetic compositions absorb or scatter ultraviolet rays of wavelength in a high energy region near 250–350 nm, by which the skin would be inflammed.

As a result of the recent progress for the study on harmfulness of ultra-violet rays, it has been found that ultraviolet rays in the UV-A region of from 320 to 400 nm, by which the skin is sun-tanned, cause blotches and freckles and promote the skin aging. Therefore, ultraviolet rays in the UV-A region, as well as ultraviolet rays in the UV-B region of from 250 to 320 nm, by which the skin is sun-burned, are considered to be harmful to the skin. In view of the above, absorbers for UV-A region ultraviolet rays was developed recently (refer to Japanese Patent Application Laid-Open No. 62517/1984).

However, these ultraviolet ray (UV-A) absorbers are organic compounds and yet involve various problems in the safety and the lasting effect thereof.

On the other hand, there have been made various studies on absorption and scattering of UV-ray and it has been known that a certain kind of inorganic powder has a great effect particularly for interrupting ultraviolet rays.

It has generally be known that powder having a higher reflective index has greater hiding power and has greater UV-ray interrupting effect. Upon measuring the optical transmittance of various metal oxides (those conventionally used for cosmetics having particle size of 0.5 m$\mu$) having a high reflective index, it was confirmed that the optical transmittance at the wavelength region from 250 to 700 nm was substantially constant (FIG. 1).

The metal oxides having an adequate UV prevention effect, thus, involve an excessive hiding power which gives unacceptable feeling to the users, so that they are not suitable as an ingredient of anti-suntan cosmetic compositions, although they are easily available.

As described above, there have not yet been provided those absorbers for ultraviolet rays in the UV-A region, which are harmless, useful, and easily and inexpensively available.

SUMMARY OF THE INVENTION

In view of the above, the present inventors have made an earnest study for developing those cosmetic compositions that can easily be available at a reduced cost, with a high safety and having a high UV-ray preventive performance in the UV-A region. We noted that zinc oxide shows an absorption, although small, at 370 nm in the measurement of the optical transmittance for metal oxides (FIG. 1) and, as a result of a further study, found that zinc oxide of a certain particle size could selectively decrease the transmittance to the light in the UV-A region and that anti-suntan cosmetic compositions having excellent transparent feeling could be obtained by incorporating such zinc oxide of a predetermined amount.

We further found that when a specific titanium oxide was incorporated in combination with the above fine particulate zinc oxide, an anti-suntan cosmetic composition which is effective for ultraviolet rays in both the UV-A region and UV-B region and excellent in the safety and in the lasting effect could be obtained.

This invention was accomplished based on the above findings, in which the first invention provides anti-suntan cosmetics compositions comprising 1 to 25% by weight of fine particulate zinc oxide having an average particle size of from 70 to 300 m$\mu$, and a second invention provides anti-suntan cosmetic compositions further containing titanium oxide having particle size of from 30 to 70 m$\mu$.

DETAILED DESCRIPTION OF THE INVENTION AND PREFERRED EMBODIMENTS

Figure 1:
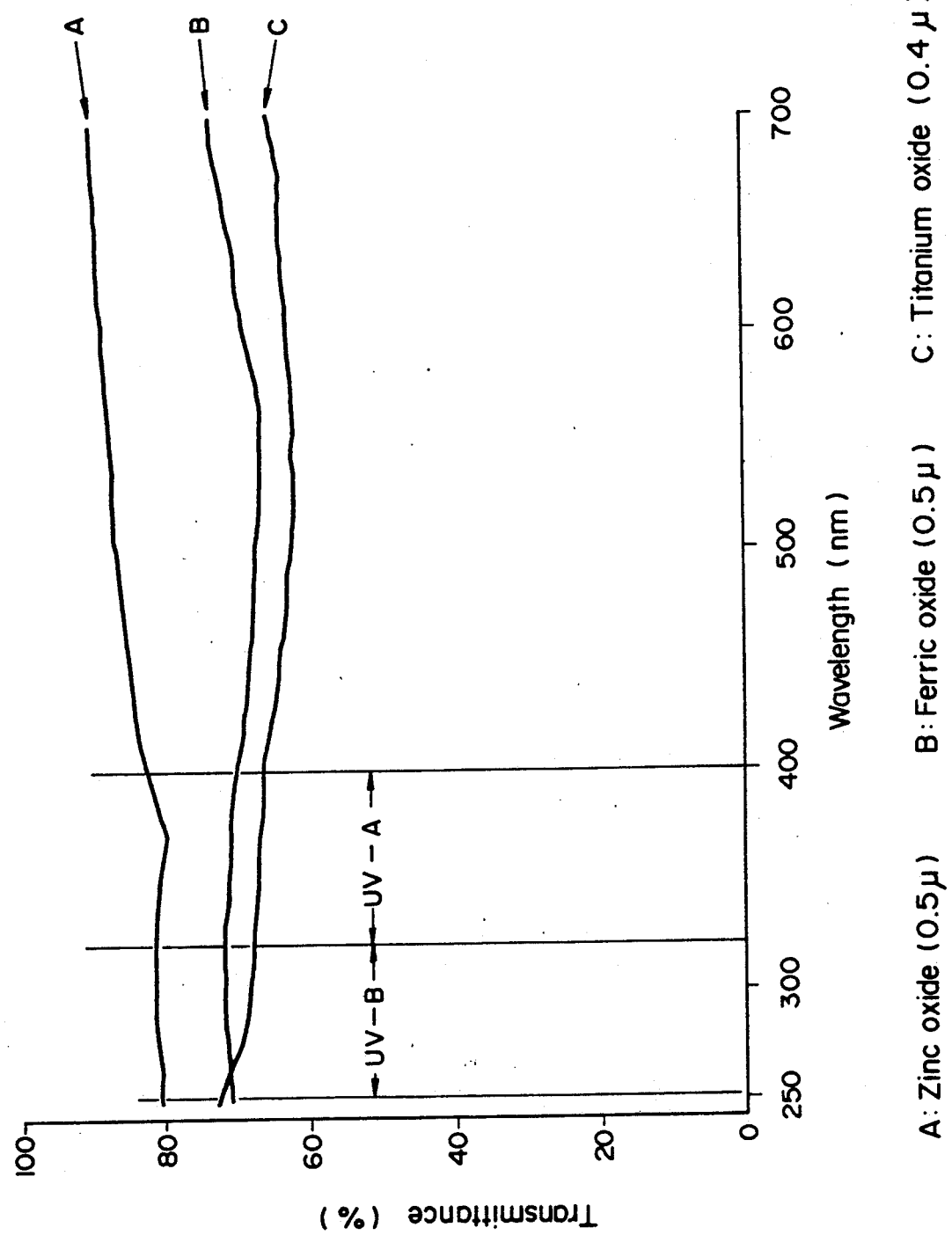
FIG. 1 is a graph showing the transmittance of various metal oxides having an average particle size of about 0.5$\mu$ against the rays of a wavelength from 250 to 700 nm.

Zinc oxide to be incorporated in the cosmetic compositions of the present invention are fine particles of an average particle size from 70 to 300 m$\mu$. The average particle size referred to in the present text is a diameter converted from the meso-pore specific surface area determined by the t-plot method (particle size converted excluding the specific surface area of micro pores of less than 20 Å). In detail, the average particle size D ($\mu$), assuming the particle as spherical form, can be obtained by the following equation:

$$D = 6/\rho S,$$

where S (m$^2$/g) represents a meso-pore specific surface area and $\rho$(g/cm$^3$) is the density.

If the particle size of the zinc oxide used in this invention is less than 70 m$\mu$, it becomes transparent (light-permeable) against the rays in both for visible and ultraviolet wave-length regions, whereas if it is greater than 300 m$\mu$, the hiding power is increased and the preventing performance for the rays in the UV-A region becomes insufficient.

Zinc oxide prepared by any known methods may be used in the present invention. The known methods are; an indirect method (French Method) in which zinc oxide is obtained by melting to evaporate metal zinc and then oxidizing it in a gas phase, a direct method (American method) in which zinc oxide is obtained by sintering and reducing zinc ores together with cokes and then oxidizing the thus obtained metal zinc, and a wet method in which a water-soluble zinc salt such as zinc chloride and zinc sulfate is used as a starting material and zinc oxide is obtained by crystallizing and sintering them. Zinc oxide of about 300 to 800 m$\mu$ and of about 600 to 700 m$\mu$ can be obtained by the direct and indirect method, respectively. The thus obtained zinc oxide may be pulverized depending on the requirement. In the case of the wet method, zinc oxide of particle size greater than 70 m$\mu$ may be obtained by controlling the crystal growing conditions. In the indirect method, those having an aimed particle size can be obtained by controlling the reaction conditions of gas phase oxidation, for example, reaction temperature, zinc concentration and oxygen concentration to be lower.

The amount of the zinc oxide to be incorporated into the cosmetic composition is from 1 to 25% by weight (hereinafter simply referred to as %) and an appropriate amount can be selected depending on the type of cosmetic composition. For instance, in the case of preparing creams, incorporation amount of from 1 to 10% is preferred in order to obtain desired effects with no rough or frictional feelings. In the case of preparing a system such as make-up cosmetics in which a great amount of powder is incorporated, from 5 to 25% of zinc oxide can be incorporated.

The particle size of titanium oxide to be used in the second invention of the present invention is preferably from 30 to 70 m$\mu$ and, the rutile type one having particle size of from 40 to 70 m$\mu$ is particularly preferred. Titanium oxide is prepared, for example, by the wet method. That is, rutile type titanium oxide may be prepared by treating ilmenite with sulfuric acid into titanium oxysulfate and calcinating meta-titanic acid obtained by hydrolyzing the titanium oxysulfate at a temperature of about 1000° C. The particle size may be controlled also by pulverization after obtaining the rutile type titanium oxide or pulverization after the hydrophobicizing treatment described later, however, it is preferred to control the particle size at the hydrolyzing step or calcinating step. The rutile type titanium oxide having an average particle size of from 40 to 70 m$\mu$ exhibits increased absorption and scattering of the rays in the UV-A region near 320 nm in addition to the rays in the UV-B region. Accordingly, in the second invention, the rays in the entire region including the UV-B region and the UV-A region can be prevented by the combined use of titanium oxide with zinc oxide having UV-A absorption at a higher wavelength near 370 nm, thereby obtaining preferable anti-suntan cosmetic compositions. Further, while titanium oxide of other crystal forms than rutile type titanium oxide such as anatase type titanium oxide has a maximum absorption wavelength in the UV-B region, the low wavelength UV-A region can also be covered to some extent by increasing the incorporation amount. These titanium oxides are used in an amount from 1 to 20% and, preferably, from 5 to 10%.

Zinc oxide and titanium oxide described above provide satisfactory effects when they are used by themselves, however these powders may be hydrophobicized by silicone oils, metal soaps, dialkyl phosphate or the likes. By the hydrophobicizing treatment, frictional feeling of zinc oxide or titanium oxide is reduced and spreadability and water proofness are improved, so that they can be dispersed stably into a base of cosmetic composition. Preferred agents for the hydrophobicizing treatment are silicone oils and, particularly, methyl hydrogen polysiloxane, dimethylpolysiloxane and the like. Treatment with the silicone oils can be carried out without causing coagulation of zinc oxide or titanium oxide particles, and the water proofness can be improved extremely.

The hydrophobicizing treatment is carried out, for example, by sufficiently mixing titanium oxide with an average particle size of from 40 to 70 m$\mu$ and silicone oils dissolved in a solvent while heating them in a low speed blender, distilling off the solvent subsequently and then applying heat treatment at 90°-450° C. The amount of the solvent (silicone oil+solvent) used herein is such that the solvent can completely sinter zinc oxide or titanium oxide, or bring them into a slurry state, preferably, in the same amount as that for zinc oxide or titanium oxide. Prior to the hydrophobicizing treatment, titanium oxide or zinc oxide may previously be treated with silica and/or alumia.

Since titanium oxide has high surface activity, it tends to coagulate and has poor dispersibility. It has also a catalytic activity, so that other cosmetic ingredients are degraded. Accordingly, hydrophobicizing treatment to titanium oxide is particularly preferred for obtaining cosmetic compositions having higher quality.

In the cosmetic compositions of this invention, a compound capable of absorbing ultraviolet rays in the UV-B region can also be incorporated. Examples of such compound include those organic compounds having maximum absorption performance at 280-320 nm, for example, 2-ethylhexyl p-methoxy cinnamate and 2-ethylhexyl p-dimethylamino benzoate. The above compound can be incorporated in an amount from 0.5 to 10% and, preferably, from 1 to 5%.

In the cosmetic compositions according to this invention, the ultraviolet absorber described above is incorporated into a cosmetic carrier to prepare into various types of cosmetic compositions.

For example, they can be prepared into foundations by incorporating loading pigment, coloring pigment, oil and shaping agent; creams by incorporating oil, water and emulsifier; lotions by incorporating oil, water, solubilizing agent and lower alcohol; and lip sticks by incorporating oil and colorant.

The commercial value of the cosmetic compositions of the present invention can further be enhanced by the addition of a humectant, perfume, anti-oxidant, corrosion inhibitor or the like.

The cosmetic compositions according to this invention can prevent human skin from blotches and freckles and suppress the aging of the skin by scattering and absorbing ultraviolet rays in the UV-A region (and UV-B region) and preventing suntan. Further, zinc oxide incorporated therein has a skin astringent effect, which is effective particularly for skin care cosmetics or cosmetics used in the summer season.

This invention will further be explained in detail referring to Examples.

EXAMPLE 1

Figure 2:
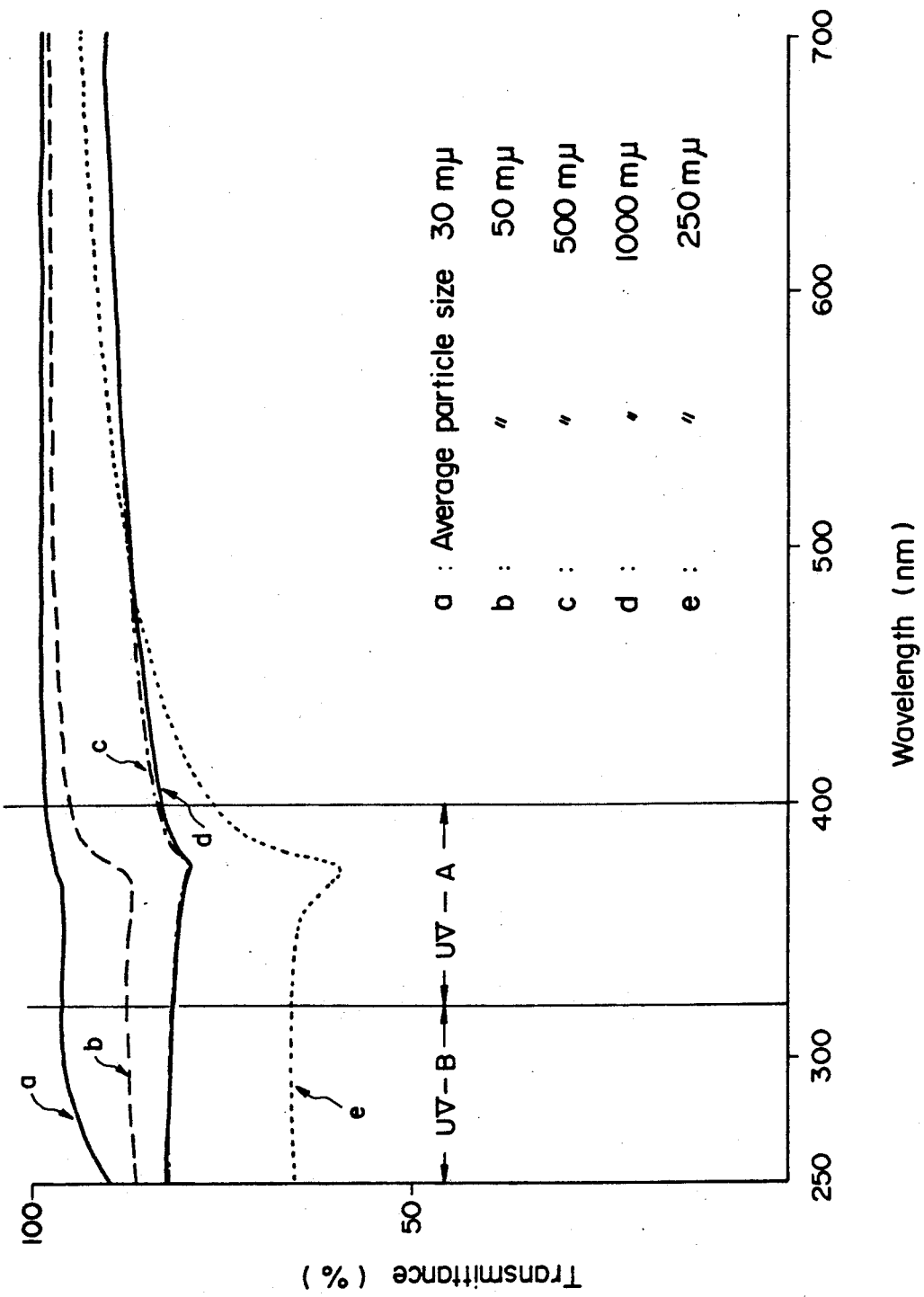
FIG. 2 is a graph showing the transmittance of zinc oxide having various particle size against the rays of a wavelength from 250 to 700 nm.

Effect of the particle size of zinc oxide to optical transmittance was examined. Zinc oxide powders having an average particle size of 30, 50, 250, 500 and 1000 mμ were dispersed each by 1% by weight in a diisostearyl malate, and then put between quartz glass cell of 0.03 mm of thickness and the optical transmittance was measured by a spectrophotometer (Model MPS 2000, manufactured by Shimazu Seisakusho). The results are shown in FIG. 2. The figure shows that zinc oxide used in this invention (average particle size of 250 mμ) has remarkably increased absorption near the wavelength at 370 nm.

EXAMPLE 2

Figure 3:
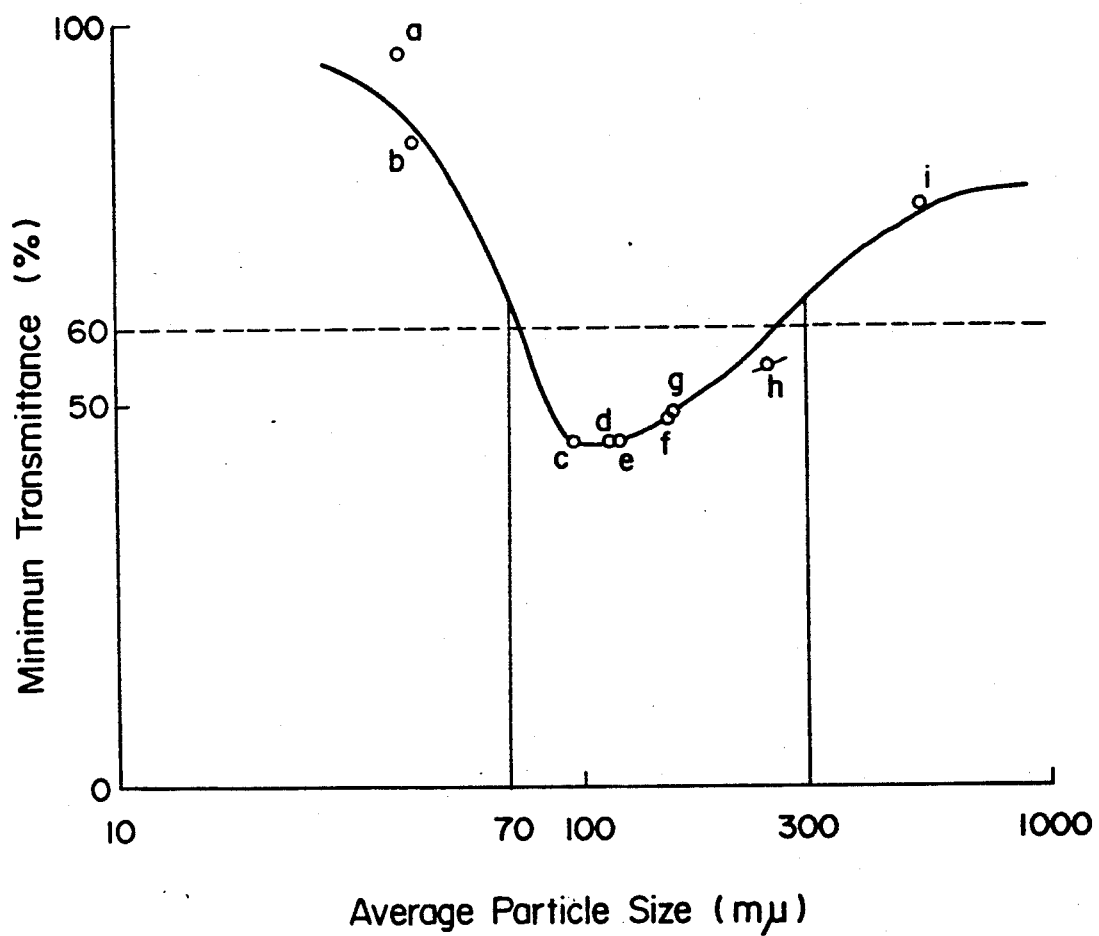
FIG. 3 is a graph showing relation between the minimum transmittance and an average particle size of zinc oxide.

The optical transmittance of zinc oxide powders shown in Table 1 below was measured. The results are shown in FIG. 3. As shown in the figure, remarkable reduction in the optical transmittance is observed at the average particle size between 70 and 300 mμ.

| Symbol | a | b | c | d | e | f | g | h | i |
|---|---|---|---|---|---|---|---|---|---|
| Product name | ZINCA-20 | ultrafine ZnO powder | EXTRAFINE GRAIN ZINC OXIDE | — | — | ultrafine zinc powder | — | — | Zinc powder No. 1 |
| Manufacturer | Sakai Kogyo K.K. | Mitsubishi Kinzoku | Sumitomo Kinzoku Kozan | — | — | Sakai Kogyo K.K. | — | — | Sakai Kogyo K.K. |
| Manufacturing method | wet method | wet method (Japanese Patent Application Laid-Open No. 205319/1982) | indirect method | same as c | same as c | indirect method followed by wet pulverization | same as c (the reaction conditions of gas phase oxidation were controlled) | indirect method followed by wet pulverization | indirect method |
| | zinc chloride ↓ zinc carbonate (calcination) ↓ zinc oxide | zinc ion solution ↓ zinc oxalate ↓ zinc oxide | metal zinc ↓ zinc oxide | (the reaction conditions of gas phase oxidation were controlled) | | | | | |
| Average particle size (mμ) | 40.7 | 44.3 | 96.4 | 114 | 120 | 156 | 157 | 250 | 527 |
| Minimum transmittance (%) | 96.0 | 84.3 | 44.7 | 44.8 | 44.7 | 48.1 | 49.2 | 55.0 | 75.8 |
| Wavelength at minimum transmittance (nm) | 360 | 364 | 370 | 370 | 370 | 372 | 372 | 372 | 373 |

Example 3
Anti-suntan lotion

| | |
|---|---|
| (1) ethanol | 10% |
| (2) glycerine | 4% |
| (3) zinc oxide: average particle size of 120 mμ (obtained by indirect method) | 3% |
| (4) titanium oxide (200–300 mμ) | 2% |
| (5) UV-absorber (2-ethylhexylparamethoxy cinnamate) | 0.5% |
| (6) camphor | 0.15% |
| (7) perfume | small amount |
| (8) purified water | appropriate amount |

Ingredients (1), (2), (5) and (7) mixed and dissolved were added to a solution prepared by dispersing the ingredients (3) and (4) into (8) containing the ingredient (6). The mixture was well agitated and prepared into a product.

Example 4
Anti-suntan cream

| | |
|---|---|
| (1) beewax | 5.5% |
| (2) cetanol | 4.5% |
| (3) hydrogenated lanoline | 7% |
| (4) squalane | 33% |
| (5) fatty acid glycerine | 3.5% |
| (6) oleophilic glycerine monostearate | 2% |
| (7) polyoxyethylene sorbitan monolaurate (20 E.O) | 2% |
| (8) zinc oxide: average particle size of 157 mμ (obtained by indirect process) | 8% |
| (9) perfume | small amount |
| (10) preservative | appropriate amount |
| (11) antioxidant | appropriate amount |
| (12) propylene glycol | 4.5% |
| (13) purified water | appropriate amount |

Ingredients (8), (10), (12) and (13) were stirred to mix and then kept at 70° C. (aqueous phase). Other ingredients were mixed and dissolved under heating and kept at 70° C. The thus obtained oil phase was added into the aqueous phase described above and the mixture was preliminarily emulsified, then emulsified by a homogenizer. The resultant emulsion was cooled down to 30° C.

Example 5
Anti-suntan powder foundation
Formulation:

| Ingredient | Example 5 | Comparative Example 1 |
|---|---|---|
| | Incorporation Amount (%) | |
| (1) mica | appropriate amount | appropriate amount |
| (2) talc | 20 | 20 |
| (3) zinc oxide: average particle size of 156 mμ (pulverizate of the product obtained by the indirect method) | 10 | — |
| (4) rutile titanium oxide: average particle size of 50 mμ | 10 | 10 |

Example 5
Anti-suntan powder foundation
Formulation:

| | Incorporation Amount (%) | |
|---|---|---|
| Ingredient | Example 5 | Comparative Example 1 |
| (5) titanium oxide: average particle size of 200-300 mµ | 8 | 8 |
| (6) iron red oxide | 0.8 | 0.8 |
| (7) yellow iron oxide | 2.5 | 2.5 |
| (8) black iron oxide | 0.1 | 0.1 |
| (9) liquid paraffin | 8 | 8 |
| (10) beewax | 2 | 2 |
| (11) preservative | appropriate amount | appropriate amount |
| (12) perfume | small amount | small amount |

Preparation method

Ingredients (1)-(8) were mixed and pulverized. They were placed in a high speed blender, to which ingredients (9)-(11) mixed and dissolved at 80° C. were further added and homogenized. Further, after admixing the ingredient (12), the mixture was again pulverized and passed through a sieve, and then compression molded onto a metal disc.

Figure 4:
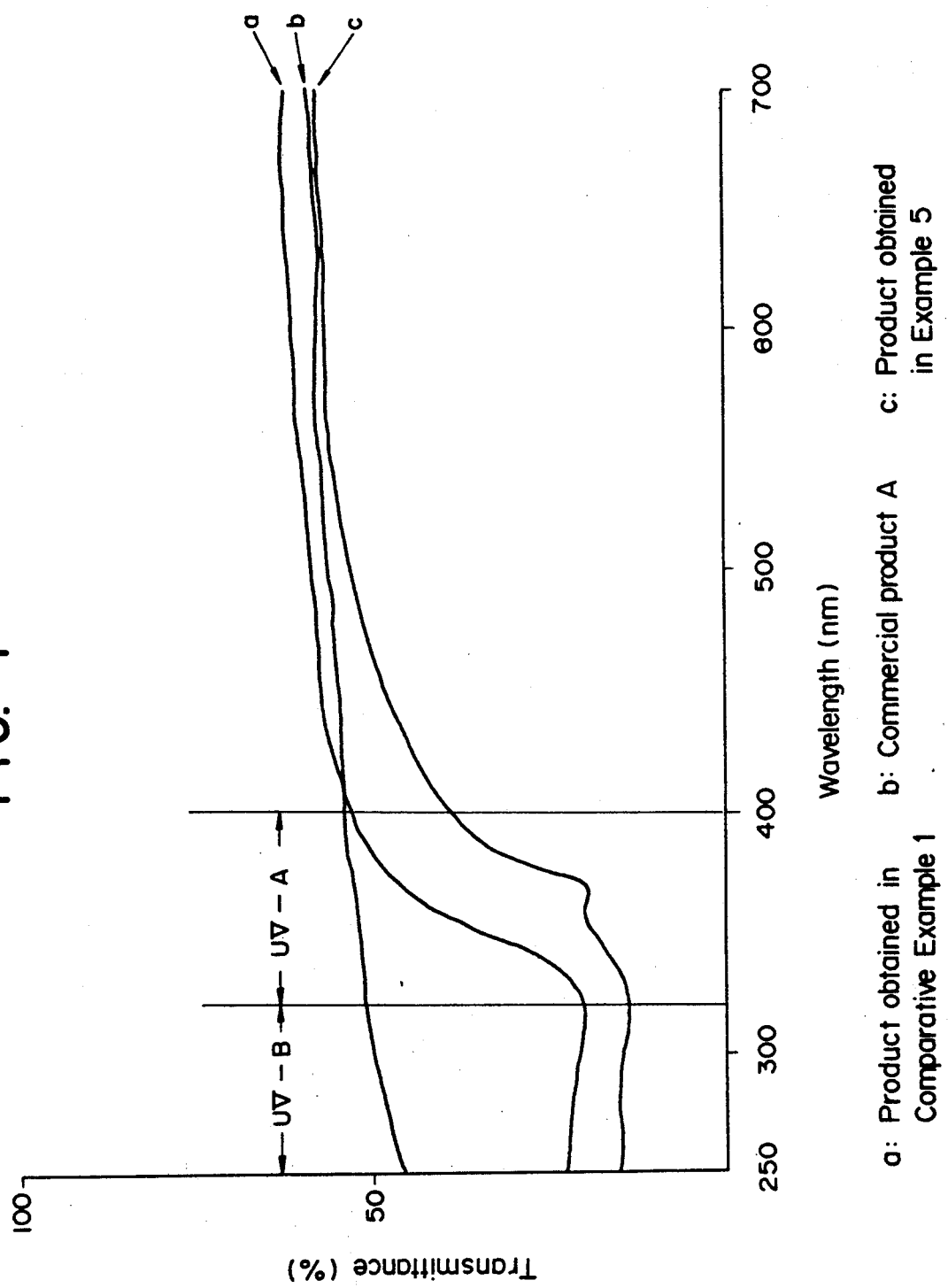
FIG. 4 is a graph showing the transmittance of each powder foundation obtained in Example 5 against the rays of a wavelength from 250 to 700 nm.

Optical transmittance was measured for the thus obtained powder foundation and commercially available product A (containing titanium oxide of 200-300 mµ and having low UV-A absorbance, used as a pigment) to the light of 250-700 nm. Upon measurement, diisostearyl malate was used as a medium, to which 10% by weight of each foundation were dispersed, put between quartz glass cells of 0.03 mm thickness and the optical transmission was measured. The results are shown in FIG. 4. As shown in the figure, the foundation of Comparative Example 1 absorbs and scatters the rays in the UV-B region causing sunburn due to the effect of titanium oxide having an average particle size of 50 mµ, while the foundation of Example 5 absorbs and scatters the rays in the UV-A and UV-B regions due to the effect of both of titanium oxide of an average particle size of 50 mµ and zinc oxide of an average particle size of 156 mµ. The foundation of Example 5 shows weak hiding power to the visible region as comparable with that of the commercially available product A.

Example 6
Creamy foundation

| | |
|---|---|
| (1) stearic acid | 5.0% |
| (2) oleophilic glycerine monostearate | 2.5% |
| (3) cetostearyl alcohol | 1% |
| (4) propylene glycol monolaurate | 3% |
| (5) squalane | 7% |
| (6) olive oil | 8% |
| (7) butyl paraoxybenzoate | appropriate amount |
| (8) purified water | appropriate amount |
| (9) triethanol amine | 1.2% |
| (10) sorbitol | 3% |
| (11) methylparaoxy benzoate | appropriate amount |
| (12) titanium oxide (200-300 mµ) | 10% |
| (13) talc | 5% |
| (14) coloring pigment (0.8% red iron oxide, 2.5% yellow iron oxide and 0.1% black iron oxide) | 3.4% |
| (15) zinc oxide having an average particle size of 128 mµ (obtained by wet method) | 11% |
| (16) perfume | small amount |

Pigment ingredients (12)-(15) were mixed and pulverized. A solution comprising a mixture of aqueous phase ingredients (8)-(11) was prepared separately, to which pulverized pigments were added and dispersed followed by heating at 75° C. The oil phase ingredients (1)-(7) heated to dissolve at 80° C. were added under stirring to the previously conditioned aqueous phase and emulsified. The emulsion was cooled under stirring and the ingredient (16) was added at 50° C. and cooled to a room temperature under stirring.

Example 7
Lip stick

| | |
|---|---|
| (1) beewax | 18% |
| (2) microcrystalline wax | 12% |
| (3) paraffin wax | 5% |
| (4) carnauba wax | 7% |
| (5) lanoline | 8% |
| (6) jojoba oil | balance |
| (7) liquid paraffin | 12% |
| (8) isopropyl palmitate | 8% |
| (9) silicon-covered titanium oxide (40 mµ) | 5% |
| (10) zinc oxide having an average particle size of 100 mµ (obtained by the indirect Process) | 5% |
| (11) colorant | appropriate amount |
| (12) antioxidant | appropriate amount |
| (13) perfume | appropriate amount |

Ingredients (9), (10) and (11) were added to a portion of the ingredient (6) and then treated in a roller mill. Ingredients (1)-(5), (7), (8) and (12) are mixed and dissolved together with the remaining portion of the ingredient (6), to which the product treated by a roller mill was added and uniformly dispersed. At the last, the ingredient (13) was added and, after mixing, poured into a dye, cooled and then the thus obtained stick was inserted into a container. The thus obtained lip stick showed high dispersibility with no sedimentation and, after coating to lips, they were less discolored.

REFERENCE EXAMPLE 1

Independent effect of scattering and absorbing the rays in the ultraviolet region and visible region of titanium oxide having an average particle size from 35 to 70 mµ used in the second invention were studied. The results are shown below.

(Measuring Method)

1% by weight of titanium oxide was dispersed in a medium, isostearyl malate, and the dispersion was put between quartz cells of 0.03 mm thickness and the transmittance at the wavelength region from 250 to 700 mµ was measured by using a spectrophotometer (Model MPS-2000 made by Shimazu Seisakusho).

(Results)

Figure 5:
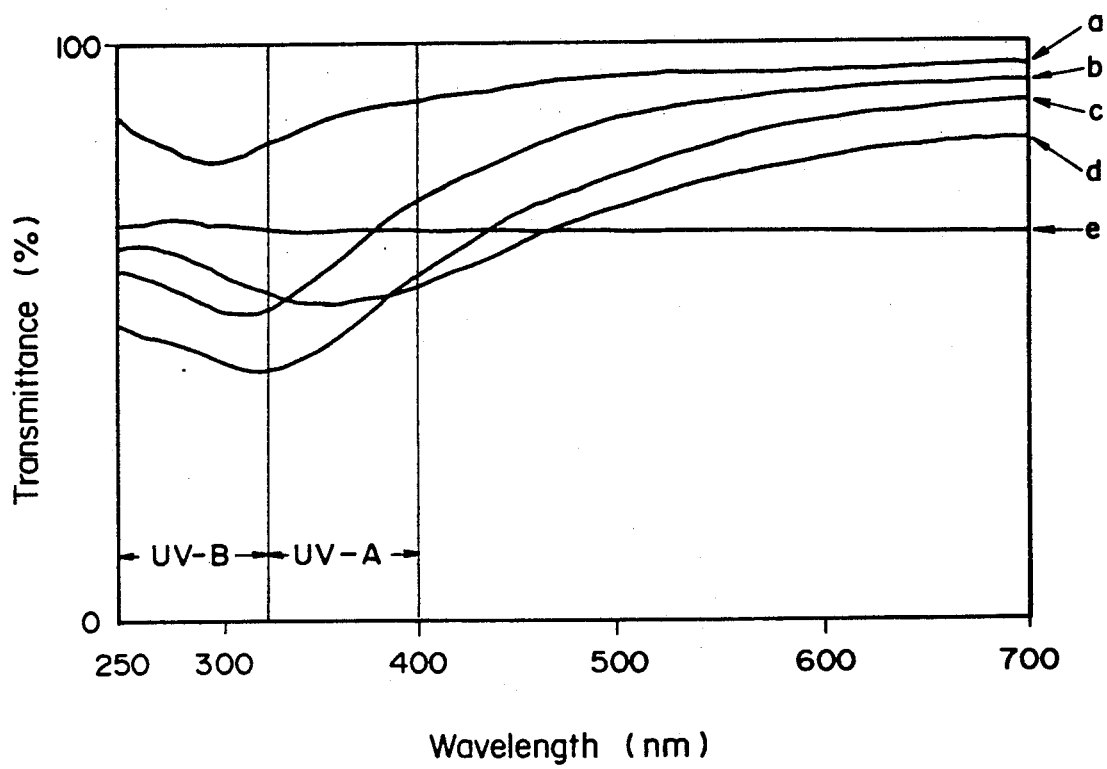
FIG. 5 is a graph showing the transmittance of titanium oxides of various particle size against the rays of a wavelength from 250 to 700 nm.

The results of the measurement are shown in FIG. 5. Titanium oxide having a large average particle size (200 mµ) showed an optical transmittance substantially equal both to the ultraviolet rays and visible rays. Titanium oxide having an extremely small average particle size (15 mµ) had a selectivity to ultraviolet rays but the effect was not sufficient. On the other hand, titanium oxide having an average particle size from 35 to 75 mµ showed selectively excellent scattering and absorbing effects particularly to ultraviolet rays at a wavelength from 290 to 350 nm, which cause intense inflammation, and had weak covering effect to the optical rays in the visible region. Among all, titanium oxide having a particle size of 50 mµ had highest interrupting effect and adequate maximum interrupting wavelength of 330 nm.

REFERENCE EXAMPLE 2

The variation of the ultraviolet ray absorbing effect of the hydrophobicized titanium oxide particles was studied and the results are shown below.

(Method)

Titanium oxide having an average particle size from 50 to 60 mµ and a hydrophobicizing agent dissolved in trichloroethylene were mixed under heating in a low speed blender. After distilling off trichloroethylene, the mixture was heated to 150° C. The effect of ultraviolet ray absorbance of the hydrophobicized titanium oxide thus obtained was measured in the same manner as described above.

(Results)

Figure 6:
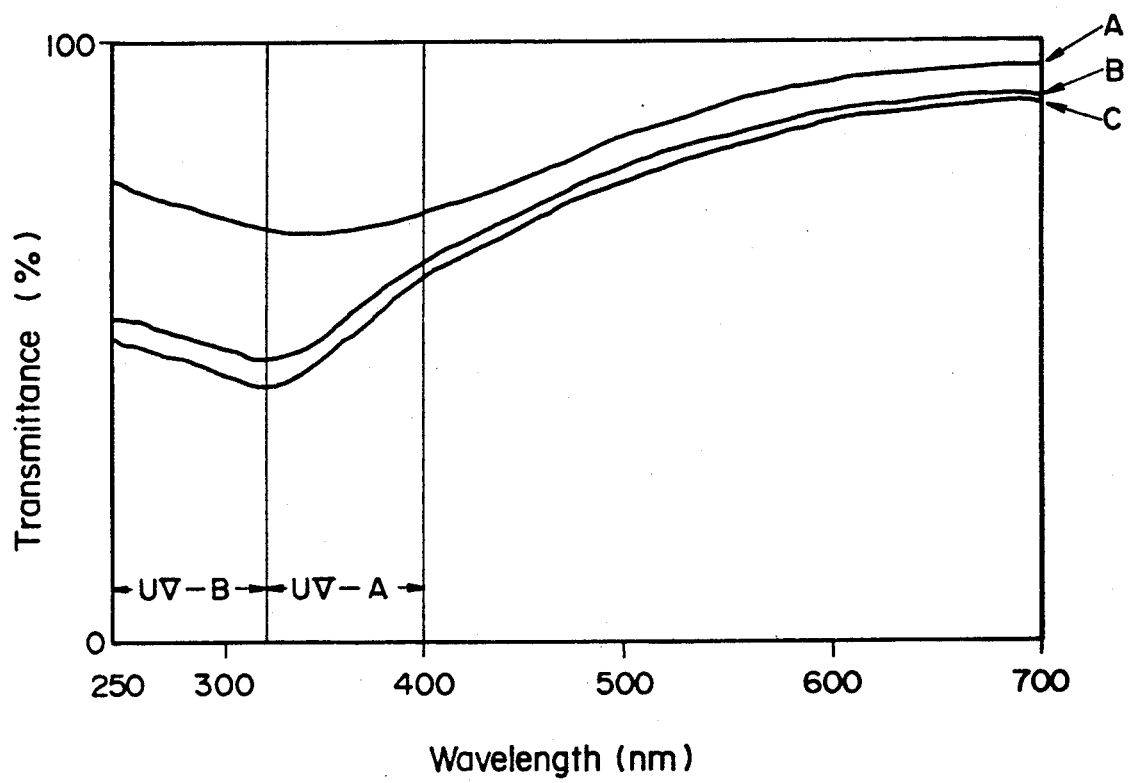
FIG. 6 is a graph showing the transmittance of hydrophobicized titanium oxide against the rays of a wavelength from 250 to 700 nm.

The results are shown in FIG. 6. FIG. 6 shows that titanium oxide treated with metal soaps was coagulated and the ultraviolet ray transmittance was increased remarkably, however titanium oxide subjected to silicon treatment (by 2% methyl hydrogen polysiloxane) possessed substantially the same ultraviolet interrupting effect as non-treated titanium oxide. Further, the thus obtained hydrophobicized titanium oxide had a reduced surface activity and extremely preferable dispersibility into a base of the cosmetic compositions.

What is claimed is:

1. An anti-suntan cosmetic composition for selectively decreasing the transmittance of the UV-A region ultraviolet rays of 320-400 nm to prevent blotches and freckles in human skin, which comprises 1-25% by weight of fine particulate zinc oxide having an average particle size of 70-300 mµ.

2. An anti-suntan cosmetic composition for selectively decreasing the transmittance of the UV-A region ultraviolet rays of 320-400 nm and the UV-B region ultraviolet rays of 250-320 nm to prevent blotches and freckles in human skin, and to suppress aging of the skin, which comprises 1-25% by weight of fine particulate titanium oxide having an average particle size of 30-70 mµ and 1-25% by weight of fine particulate zinc oxide having an average particle size of 70-300 mµ.

3. An anti-suntan cosmetic composition as defined in claim 2, wherein said fine particulate zinc oxide and/or fine particulate titanium oxide is hydrophobicized.

4. An anti-suntan cosmetic composition as defined in claim 3, wherein said hydrophobicizing treatment is carried out with methyl hydrogen polysiloxane or dimethyl polysiloxane.

5. An anti-suntan cosmetic composition as defined in claim 2, wherein said fine particulate titanium oxide is in a rutile type crystal form.

6. An anti-suntan cosmetic composition according to claim 2, wherein said titanium oxide is contained therein in an amount of from 1 to 20% by weight.

* * * * *